(12) United States Patent
Yu et al.

(10) Patent No.: US 10,583,272 B2
(45) Date of Patent: *Mar. 10, 2020

(54) STEERING ACTUATOR FOR DEFLECTABLE CATHETER

(71) Applicant: St. Jude Medical, Atrial Fibrillation Division, Inc., St. Paul, MN (US)

(72) Inventors: Alex Yu, Minneapolis, MN (US); Stephen W. Evans, Plymouth, MN (US); Genevieve L. Gallagher, Mendota Heights, MI (US); Troy T. Tegg, Elk River, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/829,202

(22) Filed: Dec. 1, 2017

(65) Prior Publication Data
US 2018/0085558 A1   Mar. 29, 2018

Related U.S. Application Data

(63) Continuation of application No. 14/272,412, filed on May 7, 2014, now Pat. No. 9,861,788.

(60) Provisional application No. 61/820,613, filed on May 7, 2013.

(51) Int. Cl.
*A61M 25/01* (2006.01)

(52) U.S. Cl.
CPC .... *A61M 25/0147* (2013.01); *A61M 25/0136* (2013.01)

(58) Field of Classification Search
CPC .................... A61M 25/0147; A61M 25/0136
See application file for complete search history.

(56) References Cited

U.S. PATENT DOCUMENTS

| 2,222,156 A | 11/1940 | Rowe | |
| 5,254,088 A * | 10/1993 | Lundquist | A61M 25/0144 600/585 |
| 5,891,088 A * | 4/1999 | Thompson | A61M 25/0136 604/524 |
| 7,717,875 B2 | 5/2010 | Knudson et al. | |

(Continued)

FOREIGN PATENT DOCUMENTS

| EP | 0521595 A2 | 1/1993 |
| EP | 0605796 A2 | 7/1994 |

(Continued)

*Primary Examiner* — Amber R Stiles
(74) *Attorney, Agent, or Firm* — Dykema Gossett PLLC

(57) ABSTRACT

Catheter shaft handles and deflection actuators are disclosed. The actuators include at least one pull wire guide wall and a means for anchoring the proximal portion of a pull wire or of a fiber attached to a pull wire. Each actuator is pivotable relative to the catheter handle housing, and may comprise at least one boss for pivoting the actuator relative to the catheter handle housing. The actuators transfer rotational motion based upon user input on a boss into longitudinal motion of a pull wire. The actuators may include a tensioning mechanism comprising a tension adjustment pin and a pin block, wherein the tension adjustment pin is rotatably attached to the pin block to enable adjustment of tension in a pull wire (e.g., during assembly of the catheter handle).

21 Claims, 15 Drawing Sheets

(56) References Cited

U.S. PATENT DOCUMENTS

| | | | |
|---|---|---|---|
| 9,861,788 B2* | 1/2018 | Yu | A61M 25/0136 |
| 2005/0288627 A1 | 12/2005 | Mogul | |
| 2006/0047245 A1 | 3/2006 | Sehra | |
| 2006/0084964 A1* | 4/2006 | Knudson | A61M 25/0122 |
| | | | 606/41 |
| 2008/0161790 A1 | 7/2008 | Dando et al. | |
| 2011/0054287 A1* | 3/2011 | Schultz | A61B 5/0422 |
| | | | 600/374 |
| 2011/0264074 A1 | 10/2011 | Tegg et al. | |
| 2013/0158379 A1* | 6/2013 | Selkee | A61B 1/0052 |
| | | | 600/373 |
| 2013/0324973 A1* | 12/2013 | Reed | A61M 25/0136 |
| | | | 604/528 |

FOREIGN PATENT DOCUMENTS

| | | |
|---|---|---|
| JP | H0838613 A | 2/1996 |
| JP | 2001054501 A | 2/2001 |
| JP | 2010094353 | 4/2010 |
| JP | 3162588 | 9/2010 |
| JP | 3162588 U | 9/2010 |
| JP | 2011010908 A | 1/2011 |
| JP | 2013017693 A | 1/2013 |
| JP | 2013153776 A | 8/2013 |
| WO | 1998041276 A1 | 9/1998 |
| WO | 2007044929 A1 | 4/2007 |

* cited by examiner

STEERING ACTUATOR FOR DEFLECTABLE CATHETER

CROSS-REFERENCE TO RELATED APPLICATIONS

This application is a continuation of U.S. application Ser. No. 14/272,412, filed 7 May 2014, which claims the benefit of U.S. provisional application No. 61/820,613, filed 7 May 2013, which are hereby incorporated by reference as though fully set forth herein.

BACKGROUND a. Field

The instant disclosure relates to steering mechanism or actuators for steerable medical devices. In particular, the instant disclosure relates to actuators in steerable medical devices employing one or more pull wires to deflect a portion of such medical devices in at least one direction and, preferably, in at least two directions.

b. Background Art

Electrophysiology catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions, and stasis of blood flow in a chamber of a heart, which can lead to a variety of symptomatic and asymptomatic ailments and even death.

Typically, a catheter is deployed and manipulated through a patient's vasculature to the intended site, for example, a site within a patient's heart. The catheter typically carries one or more electrodes that can be used for cardiac mapping or diagnosis, ablation, and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue. These lesions disrupt undesirable cardiac activation pathways and thereby limit, corral, or prevent errant conduction signals that can form the basis for arrhythmias.

To position a catheter within the body at a desired site, some type of navigation must be used, such as using mechanical steering features incorporated into the catheter (or an introducer sheath). In some examples, medical personnel may manually manipulate and/or operate the catheter using the mechanical steering features.

In order to facilitate the advancement of catheters through a patient's vasculature, the simultaneous application of torque at the proximal end of the catheter and the ability to selectively deflect the distal tip of the catheter in a desired direction can permit medical personnel to adjust the direction of advancement of the distal end of the catheter and to selectively position the distal portion of the catheter during an electrophysiological procedure. The proximal end of the catheter can be manipulated to guide the catheter through a patient's vasculature. The distal tip can be deflected by a pull wire attached at the distal end of the catheter and extending proximally to an actuator in a control handle that controls the application of tension on the pull wire.

The foregoing discussion is intended only to illustrate the present field and should not be taken as a disavowal of claim scope.

BRIEF SUMMARY

The present invention generally relates to steering actuators for deflectable medical instruments, including catheters. Representative embodiments include steerable catheters having pull wires or pull strings or tensioning members extending from a deflectable section to an actuator. The deflectable section may comprise, for example, part of a catheter shaft and may be located at or near a distal end of that catheter shaft, although the disclosure is equally applicable to devices having shaft deflection areas at any point(s) along the shaft. The actuator may be located at or near the proximal end of the catheter, typically within or on some type of handle.

In an embodiment, a steering actuator comprises (a) an inner actuator adapted to be rotatably mounted within a catheter handle housing, and (b) an outer actuator attached to the inner actuator. The inner actuator may comprise, for example, a base plate; at least one pull wire guide wall attached to the base plate and configured to pressingly engage a pull wire during at least a portion of the rotation of the inner actuator; and at least one tuner mechanism comprising a tuning pin and a pin block, wherein the tuning pin is rotatably attached to the pin block to enable initial adjustment of tension in the pull wire. The outer actuator may comprise at least one boss (e.g., a protuberance or thumb boss against with a user applies pressure).

In another embodiment, a steering actuator comprises (a) an inner actuator rotatably mounted within a catheter handle housing, and (b) a user-manipulatable actuator attached to the inner actuator to facilitate user rotation of the inner actuator. In this embodiment, the inner actuator may comprise, for example, at least one pull wire guide wall, each pull wire guide wall contoured against a respective pull wire to change the tension of the respective pull wire in response to rotation of the inner actuator; and at least one tension mechanism, each tension mechanism comprising a respective tension adjustment pin and a pin block to enable initial tension adjustment of the respective pull wire.

In yet another embodiment, a control handle comprises the following: (a) a handle housing; (b) a first curved, pull-wire-deflection surface mounted to the housing; and (c) a steering actuator at least partially sandwiched within the handle housing and configured to apply tension to a first pull wire. The steering actuator may comprise, for example, the following: (i) a first actuator component pivotably mounted within the handle housing, and (ii) a second actuator component attached to the first actuator component, the second actuator component comprising at least one boss. The first actuator component may further comprise a first pull wire guide wall configured to affect a pull wire path length traveled by the first pull wire or fiber during actuation of the steering actuator; and a first pull wire or fiber anchor. It should be noted that, in various embodiments, the first actuator component and the second actuator component comprise a unitary component. It should also be noted that, in various embodiments, an automatic or manual lock may be present and operable to releasably hold tension applied to one or more pull wires by the steering actuator. The first pull wire guide wall may comprise, for example, an arc wall section, a C-shaped wall, a U-shaped wall, a flattened-semicircular-shaped wall, a semicircular-shaped wall, or a horseshoe-shaped wall.

In another embodiment, a catheter comprises a longitudinally-extending catheter shaft comprising a proximal end portion and a distal deflectable section; a handle attached to the proximal end portion of the catheter shaft, the handle including a handle housing; a first pull wire extending along the catheter shaft and comprising a distal end portion attached to the distal deflectable section of the catheter shaft, and a proximal end portion; and a steering actuator comprising an inner actuator pivotally mounted within the handle housing and comprising a first guide wall and a first anchor point, wherein the first pull wire is attached to the first anchor point, and wherein the first guide wall is configured to affect a pull-wire-path length traveled by the first pull wire during actuation of the steering actuator whereby the steering actuator is operable to tension the first pull wire to thereby deflect the distal deflectable section of the catheter shaft.

The foregoing and other aspects, features, details, utilities, and advantages of the present invention will be apparent from reading the following description and claims, and from reviewing the accompanying drawings.

DETAILED DESCRIPTION OF THE EMBODIMENTS

Figure 1:
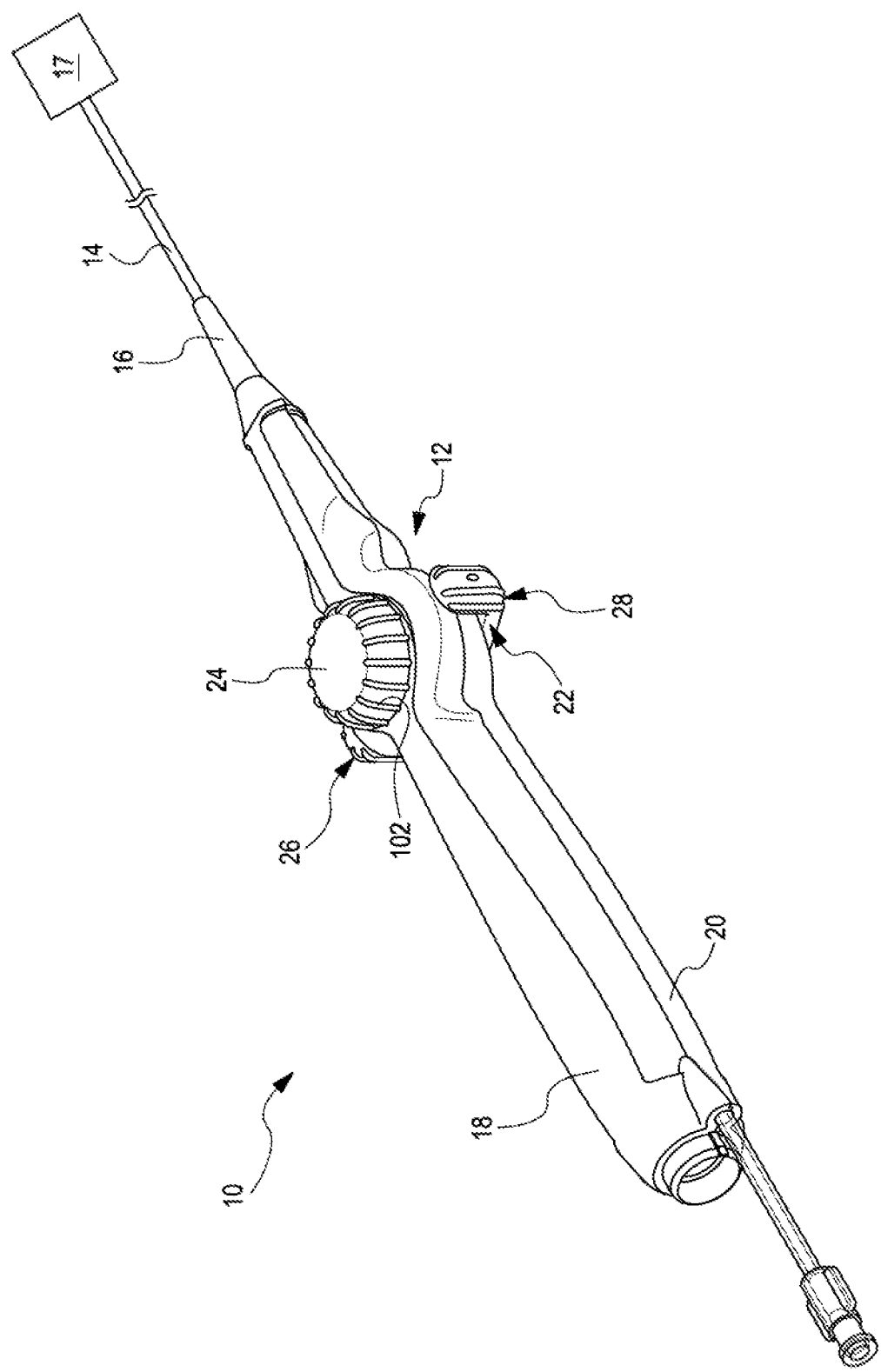
FIG. 1 is an isometric view of a catheter handle having a steering actuator for deflecting a catheter shaft.

Referring now to the figures, in which like reference numbers refer to the same or similar features in the various views, FIG. 1 is an isometric view of a catheter handle 10 comprising a steering actuator 12 for deflecting a catheter shaft 14. In FIG. 1, only a short section of a proximal end portion 15 of the catheter shaft 14 is actually depicted distal of a strain relief 16, and the deflectable section or tip of the catheter shaft is shown schematically by box 17. As shown in this figure, the handle comprises an upper handle housing 18 and a lower handle housing 20. A steering actuator 12 is pivotally sandwiched between the upper and lower handle housings, and includes an outer actuator 22 and an outer knob 24. The outer actuator 22 defines a first boss 26 and a second boss 28 that a user (e.g., an electrophysiologist or other clinician) uses to effect deflection of the catheter shaft.

Figure 2:
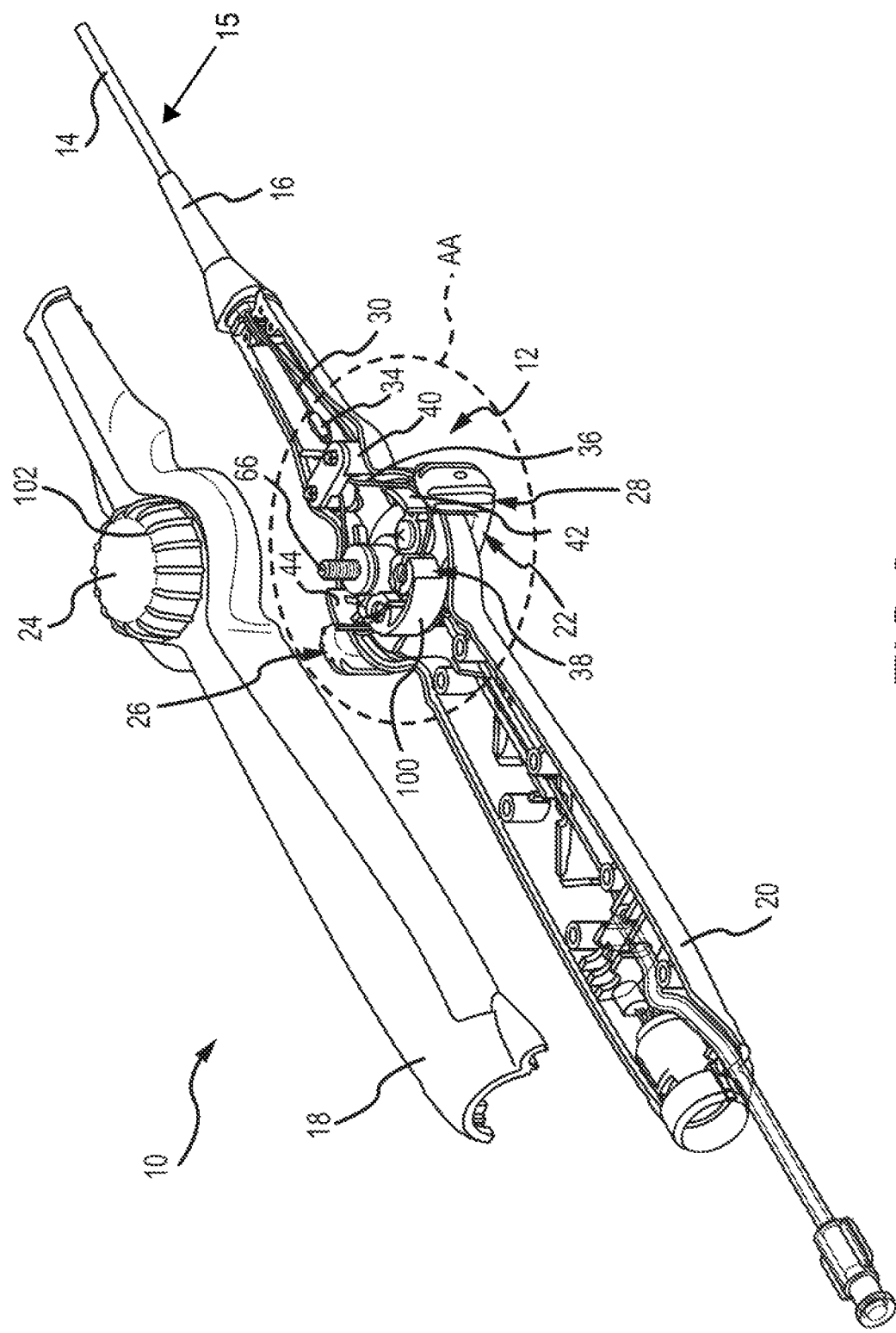
FIG. 2 is an isometric view of the catheter handle and actuator depicted in FIG. 1, but with the upper handle housing exploded away from the handle to reveal internal components of the steering actuator.

FIG. 2 also depicts the representative catheter handle 10 and steering actuator 12 shown in FIG. 1, but with the upper handle housing exploded away from the rest of the handle, revealing several components of the actuator. As shown in this figure, the proximal end portion 15 of the catheter shaft 14 is supported by a strain relief 16. Pull wires 30, 32 (both more clearly visible in FIG. 3), which extend from the handle down the catheter shaft to an anchor point (not shown) in a deflectable section (see 17 in FIG. 1) of the catheter, enter the handle from its distal end. In this embodiment, each pull wire is then attached by a connecting member, such as a crimp 34, to a fiber 36 that extends from the crimp to an anchor point 38 (e.g., a tensioning mechanism, embodiments of which are described more fully below). The fiber comprises a durable material that is selected to handle the circuitous path (and concomitant stresses) that the fiber follows from the crimp 34 to the anchor point 38. As will be discussed further below, each fiber passes over a roller 40 (or pull-wire-deflection surface), then passes around a wall section (or guide wall or pull wire guide wall) 42 before reaching one of the anchor points 38. In the embodiment shown in FIG. 2, the first and second wall sections (or guide walls) 42, 44 comprise arc wall sections or "wing wall" sections. These wall sections increase the length of the path traversed by the fiber (or a pull wire) after passing the roller on its way to the mounting point of the proximal portion of the fiber.

Figure 3:
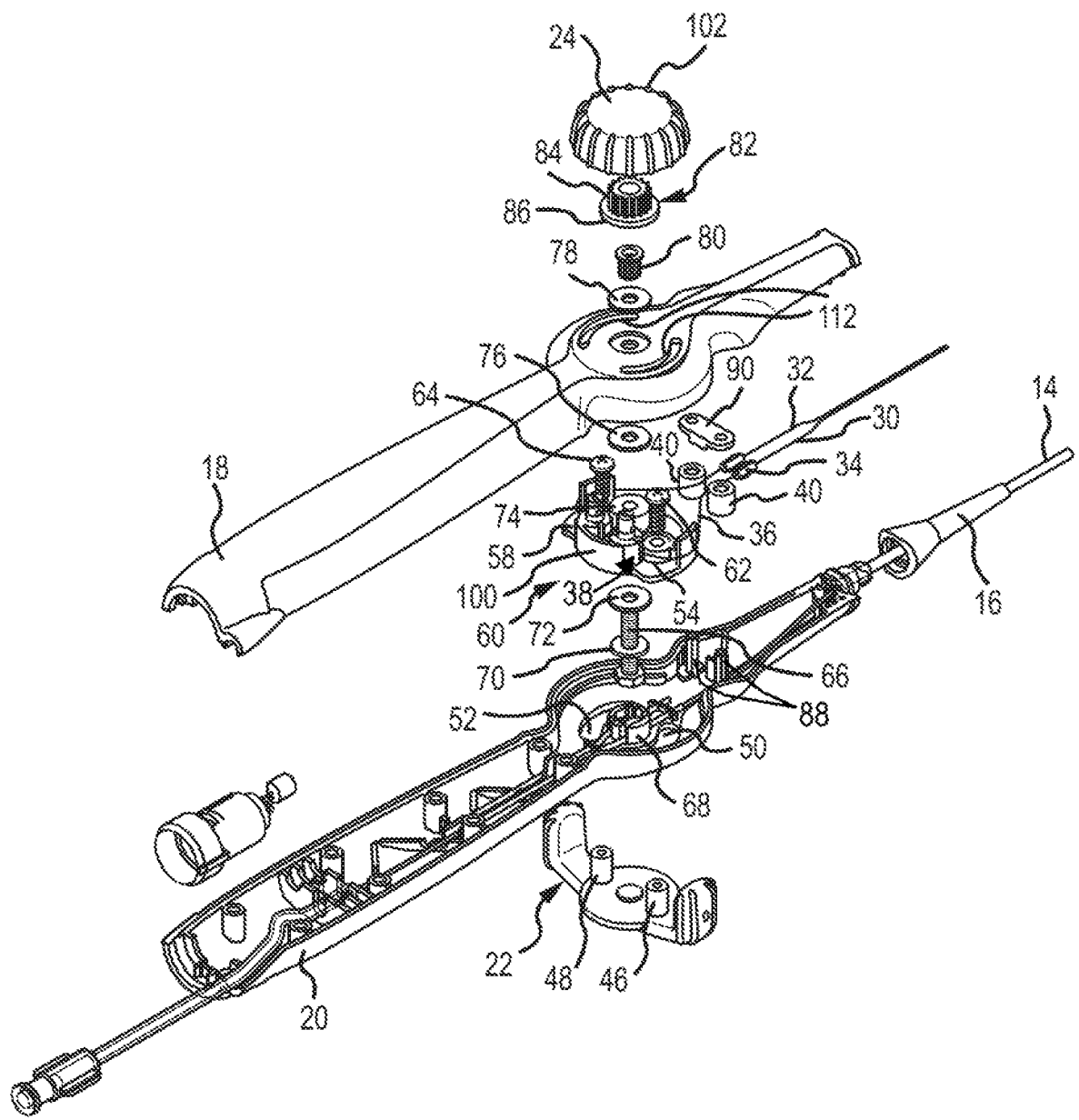
FIG. 3 is similar to FIGS. 1 and 2, but depicts several components exploded above and below the upper and lower handle housings to reveal details about the inner workings of the steering actuator.

FIG. 3 is an exploded, isometric view of the embodiment of the representative catheter handle and steering actuator shown in FIGS. 1 and 2. As may be seen toward the bottom of FIG. 3, the outer actuator 22 comprises a mounting mechanism, which is depicted as a pair of mounting posts 46, 48 in the illustrated embodiment. When the actuator is assembled with the catheter housing, these mounting posts pass through arcuate post slots 50, 52 in the lower handle housing 20, and then ride in lateral screw pillars 54, 56 (shown more clearly in FIGS. 4 and 5) that extend upwardly from a base plate 58 comprising part of the rotating inner actuator 60. The outer actuator 22 is attached to the inner actuator 60 by two mounting screws 62, 64. In particular, the shafts of the two mounting screws pass through a hole in the center of each lateral screw pillar and are threaded into a respective one of the mounting posts, which may or may not be internally threaded. The heads of the mounting screws, once the screws are installed, rest in a screw seat formed in the top surface of each lateral screw pillar.

Still looking at FIG. 3, a central hex-head screw 66 may be used to assemble the steering actuator to the handle housings. The head of this hex-head screw is retained in a head base 68 comprising part of the lower handle housing. A Belleville washer (or conical spring washer) 70 is then slid onto the shaft of the hex-head screw. The Belleville washer applies a preload to the actuator mechanism. A washer 72 (e.g., a washer made from Delrin® or another plastic material) is then placed on top of the Belleville washer, before the hex-head screw passes through a central screw pillar 74. Once the shaft of the hex-head screw passes through the central screw pillar, a PEEK washer 76 is placed on the shaft of the hex-head screw before the shaft of the screw is passed through a hole through the upper handle housing 18.

Once the shaft of the hex-head screw passes through the hole through the upper handle housing, an outer washer 78 (e.g., a stainless steel washer) is slid over the shaft of the hex-head screw. This outer washer, which may ride in a recess on the top surface of the upper handle housing, reduces friction between the inner knob and the upper handle housing. The shaft of the hex-head screw is next threaded into a threaded insert 80 which is press-fit into an inner knob 82 shown to good advantage in FIG. 3. The inner knob comprises a spur gear 84 on a base 86. The gears or splines on the spur gear of the inner knob are arranged to mesh with internal teeth or splines (see FIG. 6) on the inner surface of the outer knob.

As shown to good advantage in FIG. 3, during assembly of the catheter handle and the steering actuator, two rollers 40 are slid onto roller pins 88 and held in place by a roller retention cap or cover 90. As also shown to good advantage in FIG. 3, the two pull wires 30, 32 that are extending from a distal anchor point (not shown) at the distal end portion 17 of the catheter shaft, are attached (e.g., by the crimps shown in FIG. 3) to fibers that complete the route from the crimps to the anchor point 38 on the steering actuator. In one embodiment, the crimps 34 are implemented using titanium crimp sleeves, although any manner of coupling the pull wires 30, 32 to the fibers 36 may be utilized.

Figure 4:
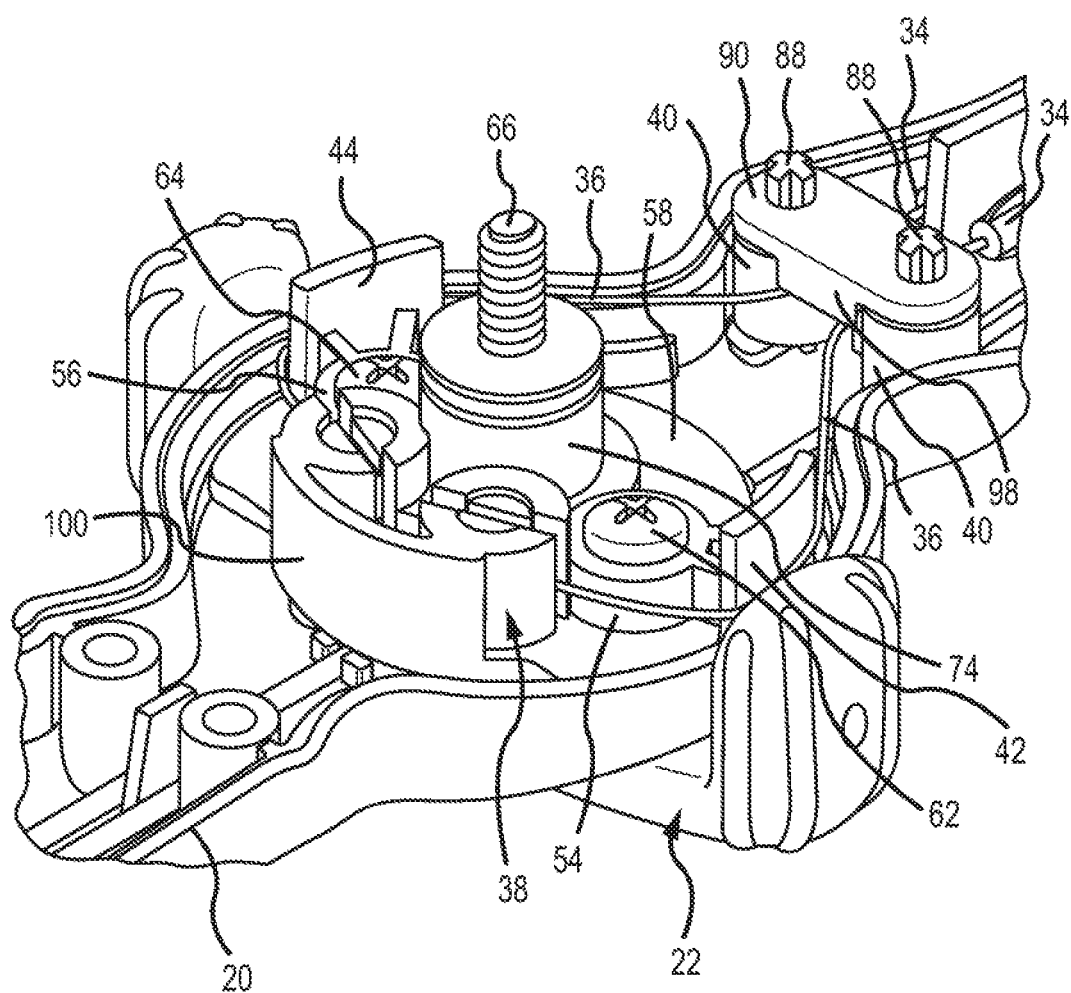
FIG. 4 is an enlarged view of the circled portion labeled AA in FIG. 2.
Figure 5:
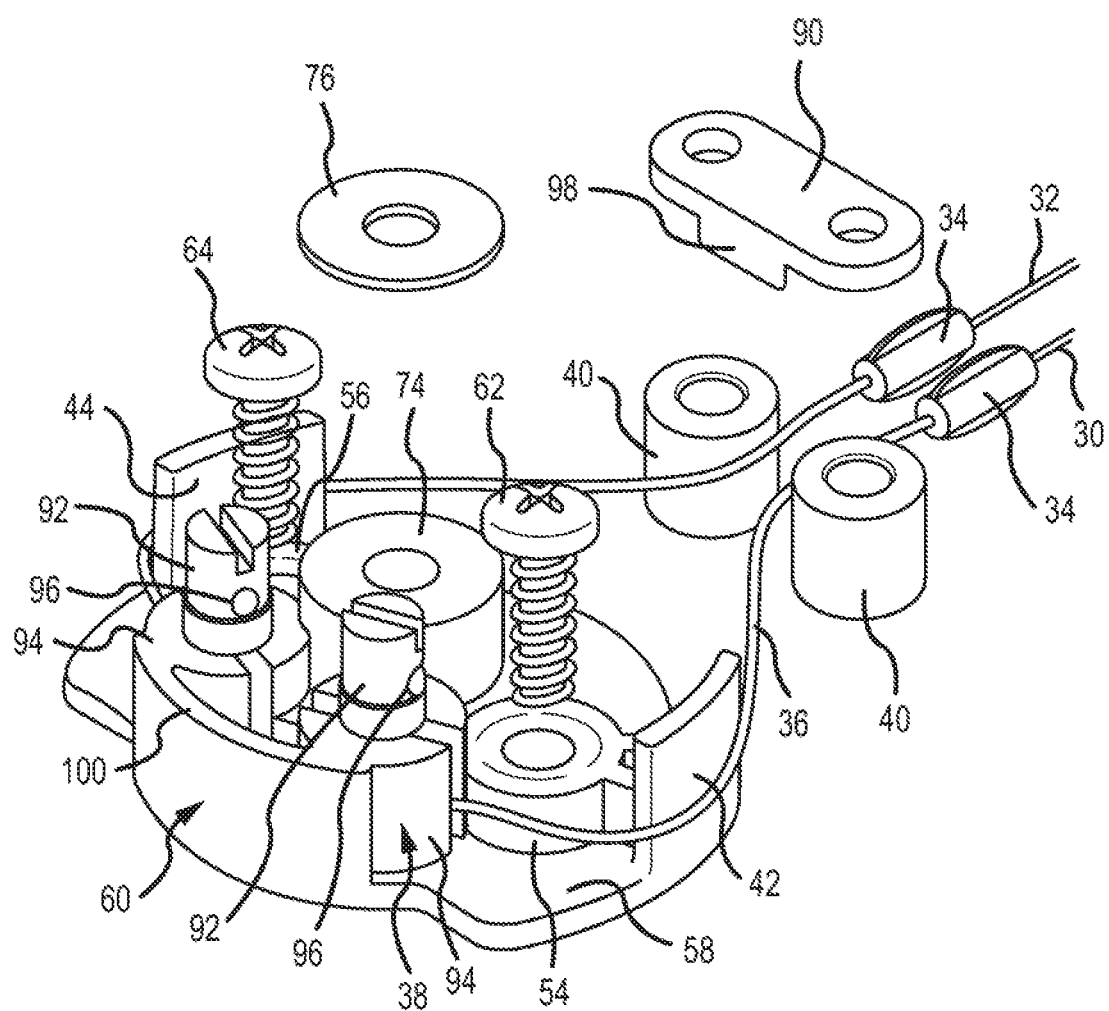
FIG. 5 is similar to FIG. 4, but depicts various components of the steering actuator spread apart to make it easier to see some aspects of the construction.

Referring next to FIGS. 4 and 5, further details of a representative inner actuator and the various components that it supports will be described. FIG. 4 is a fragmentary, isometric view of the portion of the catheter handle and steering actuator in dashed circle AA in FIG. 2. Starting at the upper right portion of this figure, it is possible to see two crimps (each labeled 34) that connect the first and second pull wires 30, 32 to the fibers (each labeled 36), respectively. Each fiber then extends around a respective roller 40 before passing around a wall section 42, 44 and then to an anchor point 38.

In this embodiment, each anchor point comprises a pull wire tensioning or tension mechanism (e.g., a pull wire "tuner mechanism" or a pull wire termination) that, in one embodiment, includes a tension adjustment pin 92 (e.g., a "tuning pin") and a pin block 94. As shown in FIGS. 4 and 5, each tension adjustment pin may be rotated into its respective pin block. The tension adjustment pins and pin blocks may include screw threads. That is, both the tension adjustment pin and the pin block comprising a tensioning mechanism may be threaded, or either the tension adjustment pin or the pin block comprising a tensioning mechanism may be threaded, or neither the tension adjustment pin nor the pin block comprising a tensioning mechanism may be threaded.

In the embodiment depicted in FIGS. 4 and 5, the pin blocks each comprise a slotted pillar. In particular, each pin block comprises a hollow cylinder with a slot or cut through opposing locations of the cylinder wall, the cut also passing through the center of the pillar. As may be seen to good advantage in FIG. 5, each tension adjustment pin comprises a fiber channel or hole 96. Each fiber is connected to the tensioning mechanism by inserting a proximal portion of the fiber into the corresponding hole or channel in the tuner pin, and then rotating the tuner pin in the pin block, which traps the fiber between the outer surface of the tuner pin and the inner surface of the pin block. The slots in the cylindrical walls of the pin blocks allow the walls to flex slightly as the fiber is wound onto a respective tuner pin. This allows the fibers, and thus the pull wires, to be preloaded with a desired tension. This system simplifies manufacturing by allowing for less precise initial trimming of the fibers (or pull wires) since adjustments can be made via the tensioning mechanisms. The tensioning mechanisms allow for easy termination of the fiber ends and permit precise preloading of desired tension on the pull wires.

As also may be seen to good advantage in FIG. 4, the roller retention cap 90 includes a guide wall 98 that extends downwardly (as depicted in FIG. 4) to keep the fibers at a desired trajectory toward the first and second guide wall sections. As may also be seen to good advantage in FIG. 4, each roller pin 88 has a cross-sectional area in the shape of a cross, for example, rather than a circle. This cross-sectional shape for the roller pins helps reduce friction between the outer surface of the roller pins and the inner surface of the rollers. It should be noted that each roller may be replaced with a fixed cylinder that does not rotate on a roller pin, or by an arcuate guiding surface configured to guide one of the fibers on the desired trajectory toward its respective wall sections. It should also be kept in mind that each of the pull wires could traverse the entire course from its anchor point at the distal end of the catheter to its anchor point in the handle (e.g., at one of the tensioning mechanisms shown to best advantage in FIGS. 4 and 5).

As may also be seen in FIGS. 2-5, the inner actuator may include a rear wall section 100. The rear wall section shown in these four figures is an arcuate wall. This wall section may, for example, provide some structural integrity to the inner actuator.

Figure 6:
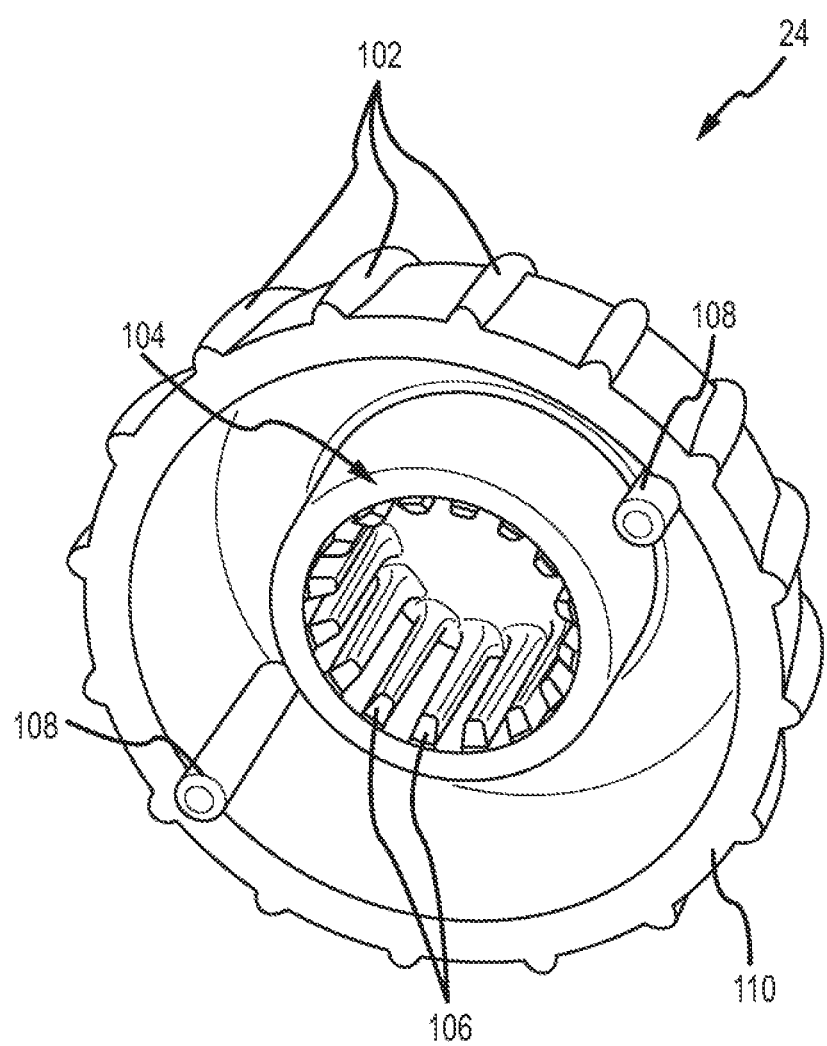
FIG. 6 is an isometric view looking at the underside of the outer knob of the actuator, depicting the splines or teeth of the internal gear comprising part of the outer knob.

FIG. 6 is an isometric view showing the underside of a representative outer knob 24. As may be clearly seen in this figure (and in FIGS. 1-3), the outer surface of the outer knob may comprise ridges 102 to facilitate grasping of the outer knob during use of the catheter comprising a steering actuator. The outer knob also includes on its interior an internal gear 104, comprising splines or teeth 106 configured to mesh with the splines or teeth on the outer surface of the inner knob 82 shown in FIG. 3. FIG. 6 also clearly depicts two limit posts 108 extending downwardly past a lower surface 110 of the outer knob. These limit posts are designed to ride in travel confinement channels 112 shown to good advantage in FIG. 3 and permit the outer knob, in this embodiment, to be twisted or turned up to 90 degrees.

During assembly of the catheter handle housing and steering actuator, the inner knob 82 may be tightened onto the hex-head screw 66 in order to create a desired amount of preloading (internal friction) in the handle. This preloading makes it possible for the deflected catheter to maintain (or nearly maintain) a deflected configuration without the user having to maintain force (or as much force) on the bosses. Once a desired amount of preloading is set, the outer knob is attached over the inner knob with each limit post centered longitudinally and laterally in its respective travel confinement channel. Being able to put the outer knob in multiple positions on the inner knob enables the described calibration of the actuator.

With the limit posts 108 riding in their travel confinement channels 112, the device may be 'locked' while limiting the locking force that an operator can apply, preventing that locking force from going higher than needed to keep the actuator in place. Without the limit posts, the operator could keep turning the outer knob, possibly inadvertently over-rotating the outer knob and thereby putting excessive tension on the actuator mechanism and pull wires. Another way to implement the "stop" feature is to provide a hole in the outer knob, and then, when the outer knob is in the right place, snap a pin through the hole.

When the outer knob 24 is turned during use of the catheter, that turns the inner knob 82, which lifts the hex-head screw 66 without rotating the screw itself. That, in turn, compresses or pinches the inner actuator between the Delrin® washer 72 and the PEEK washer 76, generating friction to stop the inner actuator from moving, which, for example, holds the distal end of a catheter shaft in a deflected configuration.

Figure 7:
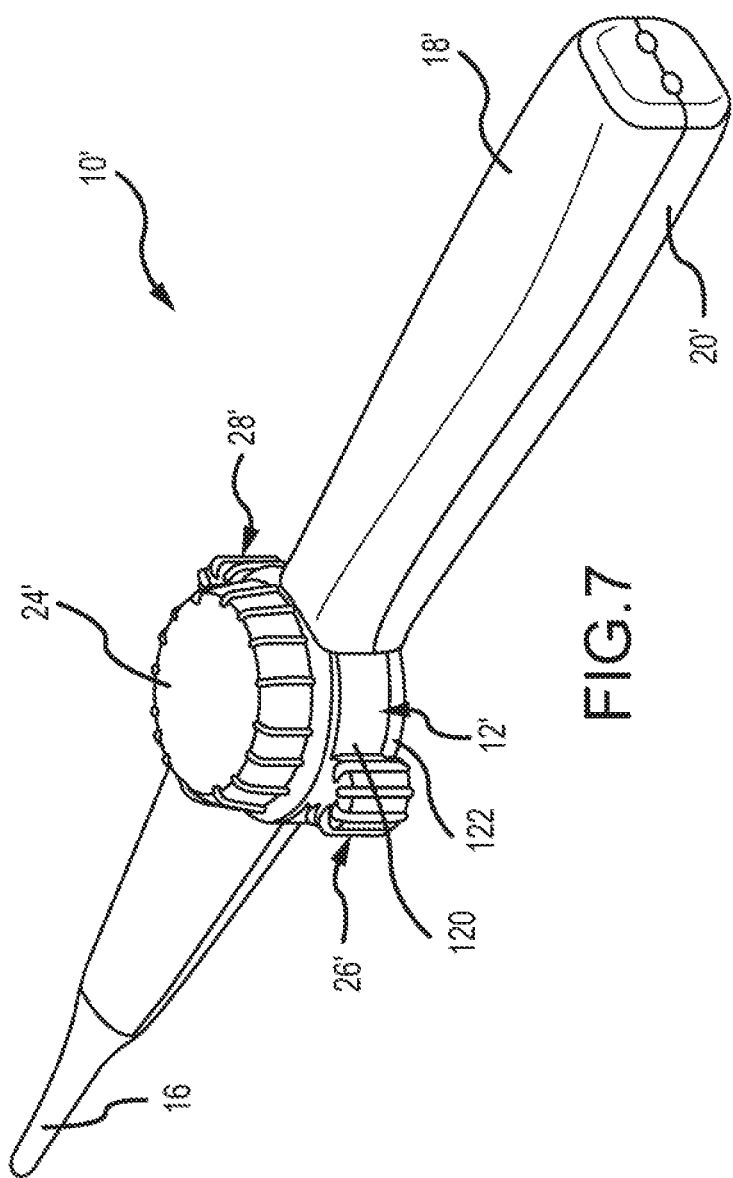
FIG. 7 is similar to FIG. 1, but depicts another catheter handle, including an alternative steering actuator for deflecting a catheter shaft.

FIG. 7 depicts an alternative embodiment of a catheter handle 10' and steering actuator 12' for deflecting a catheter shaft. This embodiment again includes an upper handle housing 18', a lower handle housing 20', an outer knob 24', and a strain relief 16. The actuator according to this embodiment is different from the actuator discussed above, and includes an upper actuator 120 and a lower actuator 122. It also includes a first boss 26' and a second boss 28'.

Figure 8:
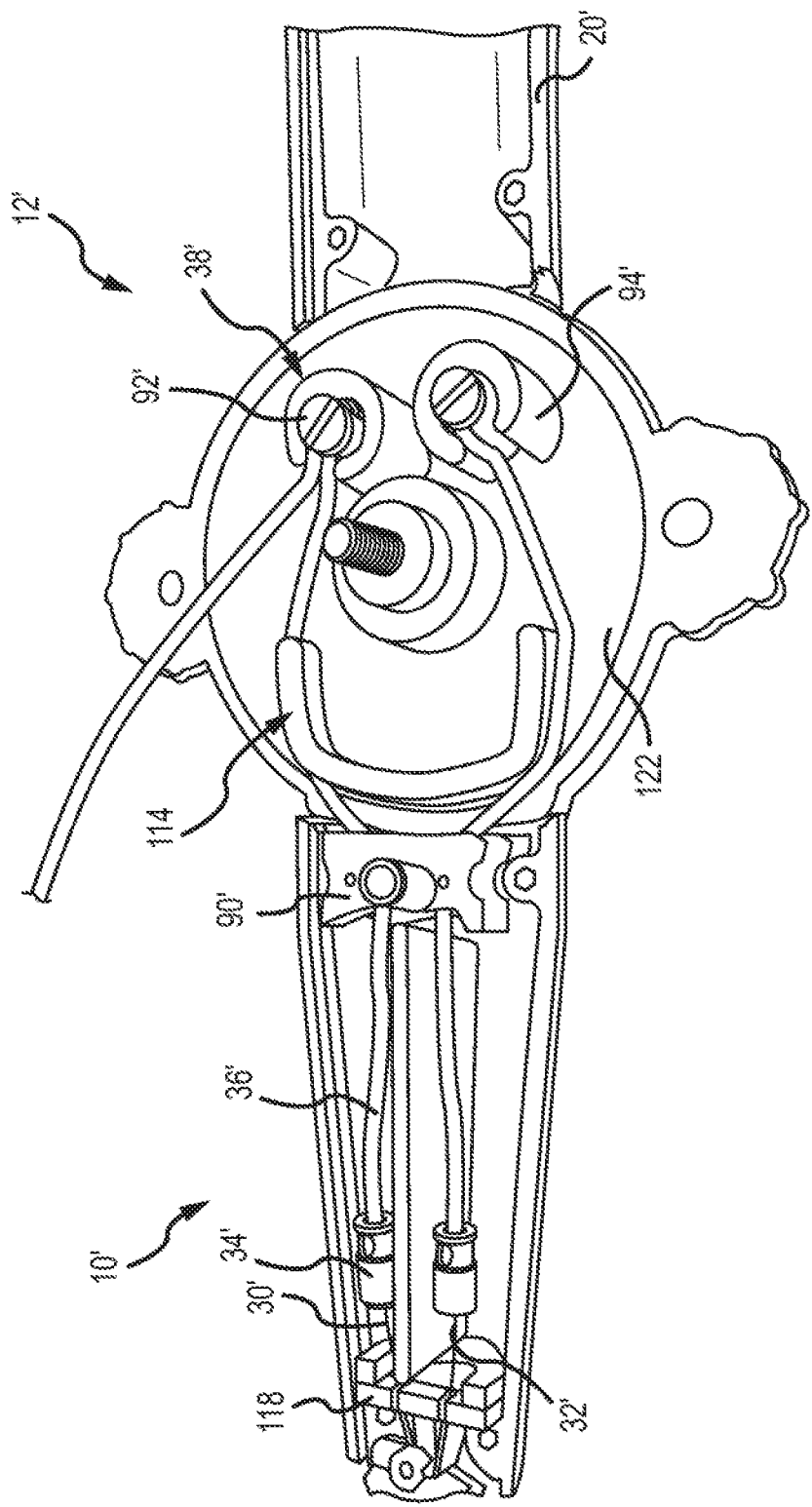
FIG. 8 is a fragmentary, isometric view of the catheter handle and steering actuator depicted in FIG. 7, but with the upper handle housing removed to reveal several components of the steering actuator.

FIG. 8 is a fragmentary, isometric view of the catheter handle and steering actuator depicted in FIG. 7, with the upper handle housing removed and with the upper actuator 120 removed to reveal details about the steering actuator. As oriented in FIG. 8, the steering wires enter the handle from the left side of the figure. The distal ends (not shown) of the pull wires would be anchored to a deflectable catheter shaft section (see, for example, distal deflectable section 17 in FIG. 1) at or near a distal end of the catheter. The proximal end of each pull wire, as depicted in FIG. 8, is attached to a corresponding fiber 36' via a crimp 34'. In all of the disclosed embodiments, alternative techniques could be used to attach each pull wire to its respective fiber, or each pull wire could extend the entire length from its distal anchor point (not shown) to its proximal anchor point.

The steering actuator depicted in FIG. 8 is similar to the actuator described above. However, in this embodiment, a single, C-shaped or U-shaped (or flattened-semicircular-shaped or horseshoe-shaped) guide wall 114 is present. The shape of the guide wall 114 may be any shape that enables the fiber/pull wire to be taken up or let out upon manipulation of the actuator (e.g., rotation of the inner actuator in this embodiment), For example, the front wall of the illustrated U-shaped guide wall 114 could be removed in whole or in part, while the side portions of the guide wall 114 are used to further tension or relax their respective pull wires when the actuator is rotated one way or the other. The shape of the guide wall 114 allows the fiber (or pull wire if no fiber is used) to follow a fairly straight path. This helps reduce bending of the fiber (or pull wire). When the actuator is rotated in the handle housing during use of the catheter, the fiber starts wrapping at the outer radius, and not at the flattened sides. Thus, the travel gain is on the outside radius of the guide wall. The outer radius of the guide wall is at the same radial distance as if the guide wall were semicircular.

In the steering actuator depicted in FIG. 8, each of the fibers passes a rotatable roller or fixed roller or curved surface (not visible in FIG. 8, but located under the retention cap 90'), then passes by the guide wall 114 before angling toward an anchor point comprising an alternative tensioning mechanism 38'. In this embodiment, the tensioning mechanisms again comprise a pair of tension adjustment pins 92' mounted in pin blocks 94'. In this embodiment, however, each pin block only has a single slot, whereas each pin block depicted in, for example, FIGS. 4 and 5, included a pair of slots. The pin blocks again comprise an integral part of, or are mounted on, a rotating lower actuator 122. Preferably, each tuner pin 92' again includes a fiber hole to facilitate attaching the fiber to the tuner pin prior to "tuning" (i.e., tensioning) the pull wire.

Figure 9:
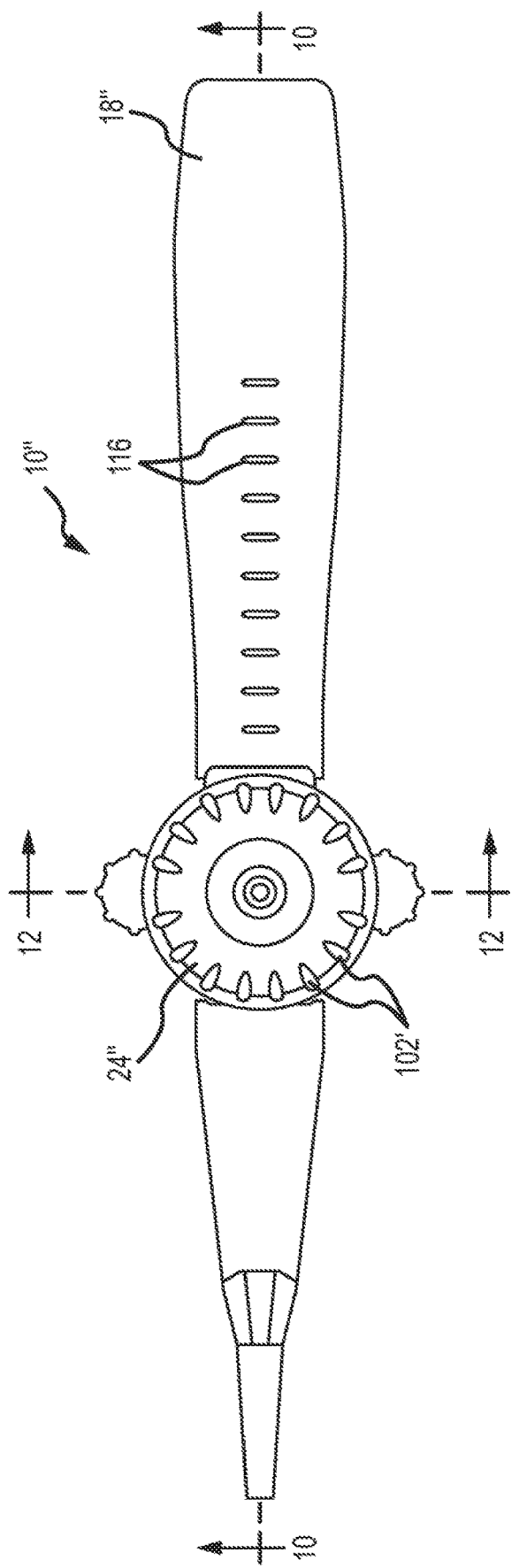
FIG. 9 is a top view of a catheter handle including a steering actuator for deflecting a catheter shaft.

FIG. 9 is a top view of a catheter handle 10" and steering actuator similar to the catheter handle 10' and steering actuator depicted in FIGS. 7 and 8, but shows a slightly different configuration for the outer knob 24" and for the top surface of the upper handle housing 18". In particular, in the configuration depicted in FIG. 9, the ridges 102' around the circumference of the outer knob extend further onto the top surface of the outer knob, and the outer surface of the upper handle housing includes a plurality of lateral ridges 116 to enhance the gripability of the handle.

Figure 10:
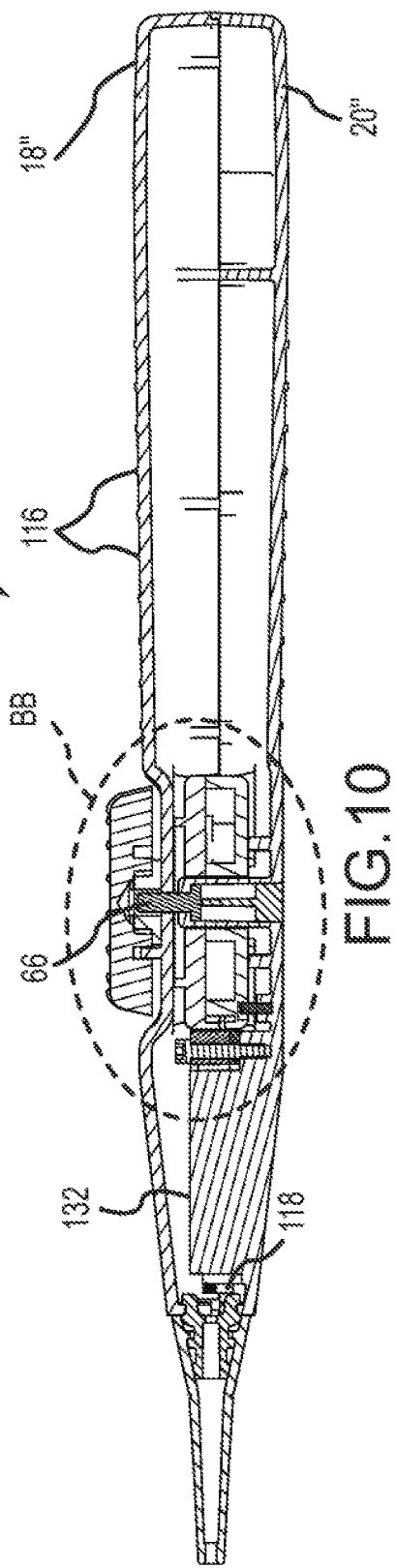
FIG. 10 is a longitudinal cross-sectional view taken along line 10-10 of FIG. 9.
Figure 11:
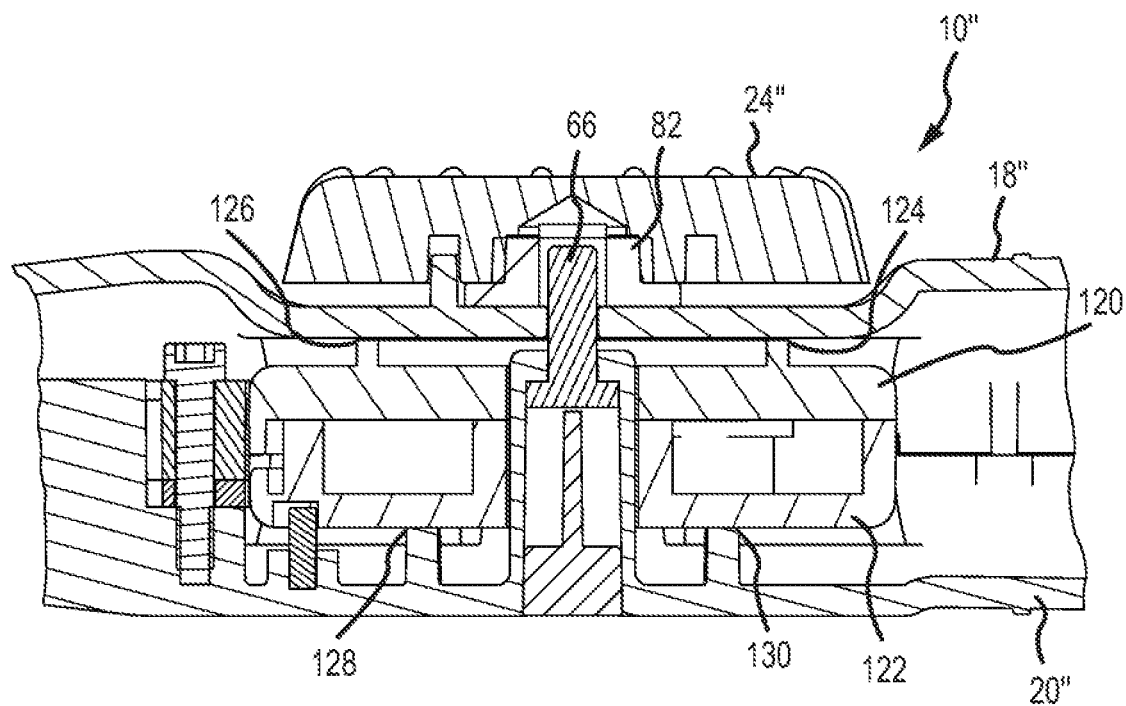
FIG. 11 is an enlarged view of the circled portion labeled BB in FIG. 10.
Figure 12:
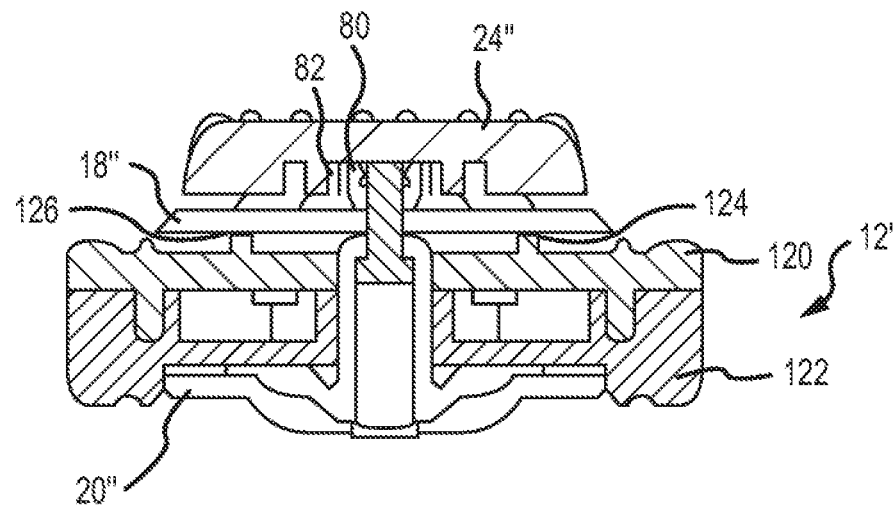
FIG. 12 is a cross-sectional view taken through the center of the steering actuator, along line 12-12 of FIG. 9.

Looking next at FIGS. 10-12, additional aspects of the steering actuator also depicted in FIGS. 7-9 will be described. FIG. 10 is a cross-sectional view taken along line 10-10 of FIG. 9 and FIG. 11 is an enlarged view of the region in dashed circle BB of FIG. 10. A coil stop 118 may be seen in FIG. 10 (see also FIG. 13). In particular, the pull wires may be surrounded by coils (not shown) in at least a portion of the catheter shaft. The proximal end of the coils rests against the distal side of the coil stop, and the pull wires extend from the coil stop proximally into the handle without being surrounded by the coils.

In the assembled steering actuator, a number of friction points exist, by design, between the steering actuator and the upper and lower handle housings 18", 20". When the hex-head machine screw 66 is pulled upwardly by the inner knob 82 and its threaded insert, this creates an increasing amount of friction between, for example, the upper actuator 120 and the upper handle housing 18" at, for example, the identified friction points 124, 126 and between, for example, the lower actuator 122 and the lower handle housing 20" at, for example, the identified friction points 128, 130. As previously discussed, the handle may be preloaded to a desired amount of internal friction (which helps keep the catheter in a deflected state after a user inputs a deflection force) by threading the inner knob onto the hex-head machine screw prior to placing the outer knob onto the inner knob. Once the desired amount of preloading has been achieved, the outer knob is mounted on the inner knob. The user then, as also previously discussed, is able to rotate the outer knob to create sufficient friction between the handle housing and the actuator to temporarily 'lock' the distal end of the catheter in a desired deflected configuration.

Figure 13:
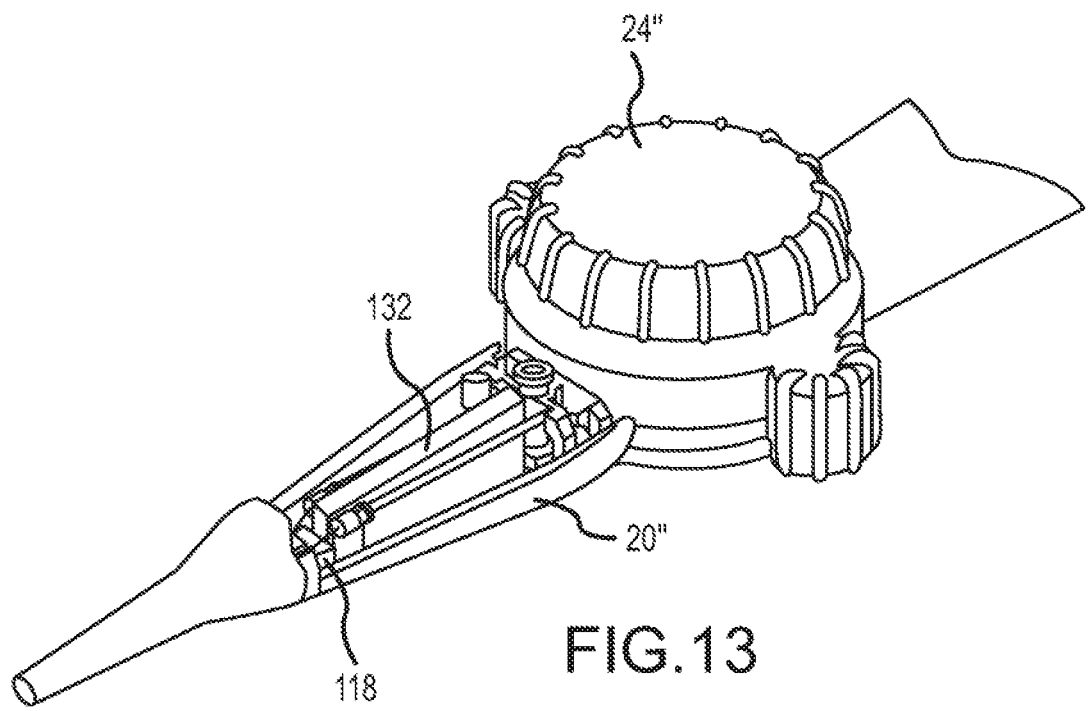
FIG. 13 is a fragmentary, isometric view of a portion of the left side and top of the catheter handle and actuator depicted in FIGS. 7-12 with the front portion of the upper handle housing removed to reveal various internal components.

FIG. 13 is a fragmentary, isometric view of a portion of the catheter handle and steering mechanism depicted in FIGS. 7-12, but with a portion of the upper handle housing removed to reveal components in the distal part of the handle. As may be clearly seen in FIG. 13, a separation wall 132 may extend longitudinally from adjacent to the coil stop to a location just distal to the steering actuator. The separation wall, if present, helps isolate the pull wires or their respective fibers to keep them from interfering with each other during operation of the steering actuator. The separation wall can also provide structural integrity to the handle.

Figure 14:
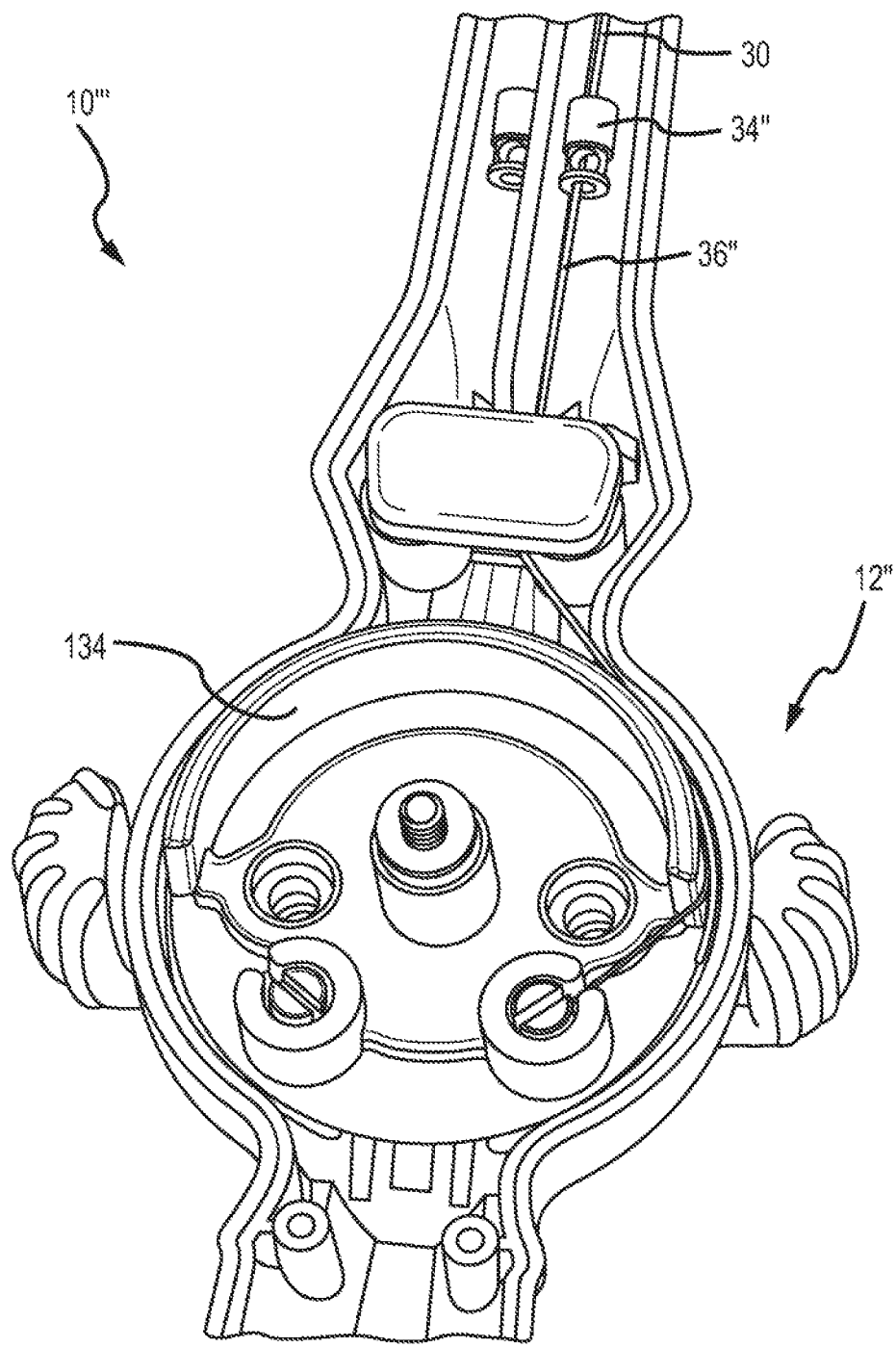
FIG. 14 is a fragmentary, isometric view of a catheter handle and steering actuator comprising an alternative, forward-facing guide wall.

FIG. 14 is a fragmentary, isometric view of a catheter handle 10''' and steering actuator 12'' according to another embodiment. In this embodiment, the guide wall 134 is a forward-facing guide wall (i.e., it curves or bows forward) that extends in a semicircle from approximately the nine o'clock position on the left of FIG. 14, through the twelve o'clock position, and to the three o'clock position, as oriented in FIG. 14. Similar to what is depicted in the figures already described, the pull wires 30, 32 enter from the distal end of the handle (not shown in FIG. 14). At the top of FIG. 14, a pull wire is shown entering a crimp connector 34'', which it will be joined to a fiber 36''. The fiber then extends proximally past a roller, around a portion of the semicircular guide wall, and then to a tensioning mechanism similar to one of the tensioning mechanisms described above. For simplicity, FIG. 14 only depicts a single pull wire connected to a single fiber. If a single pull wire is used in the completed handle in any of the embodiments depicted and described herein, the catheter handle would be a unidirectional handle. Each of the configurations shown and described herein could be configured for bidirectional or unidirectional steering of the catheter shaft.

Figure 15:
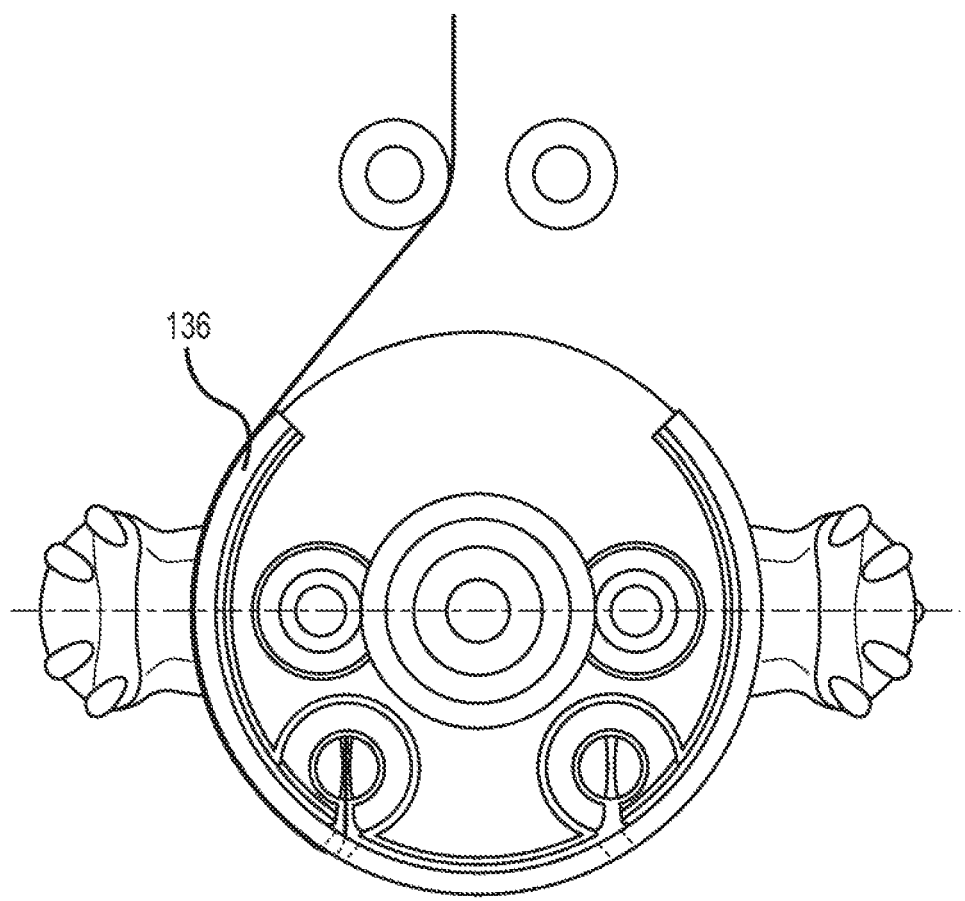
FIGS. 15-17 schematically depict a portion of another embodiment of a steering actuator comprising an alternative, rearward-facing guide wall.
Figure 16:
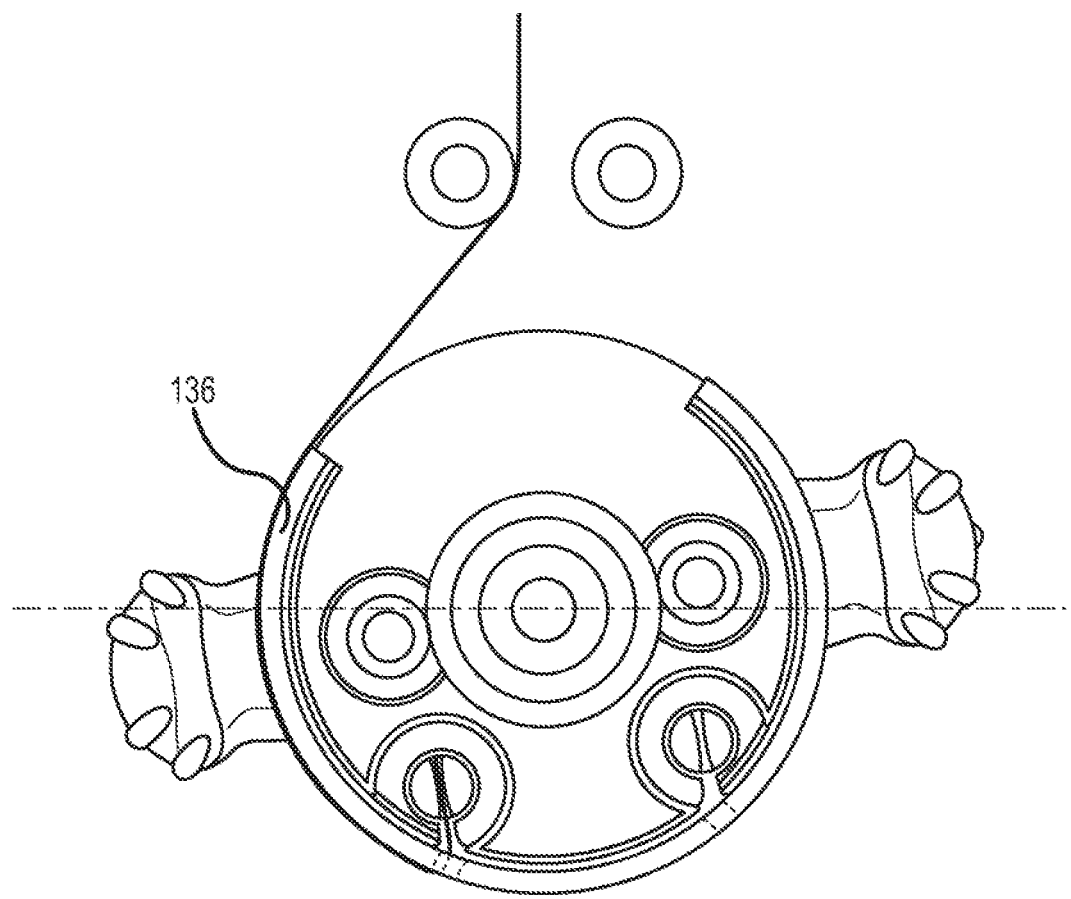
Figure 17:
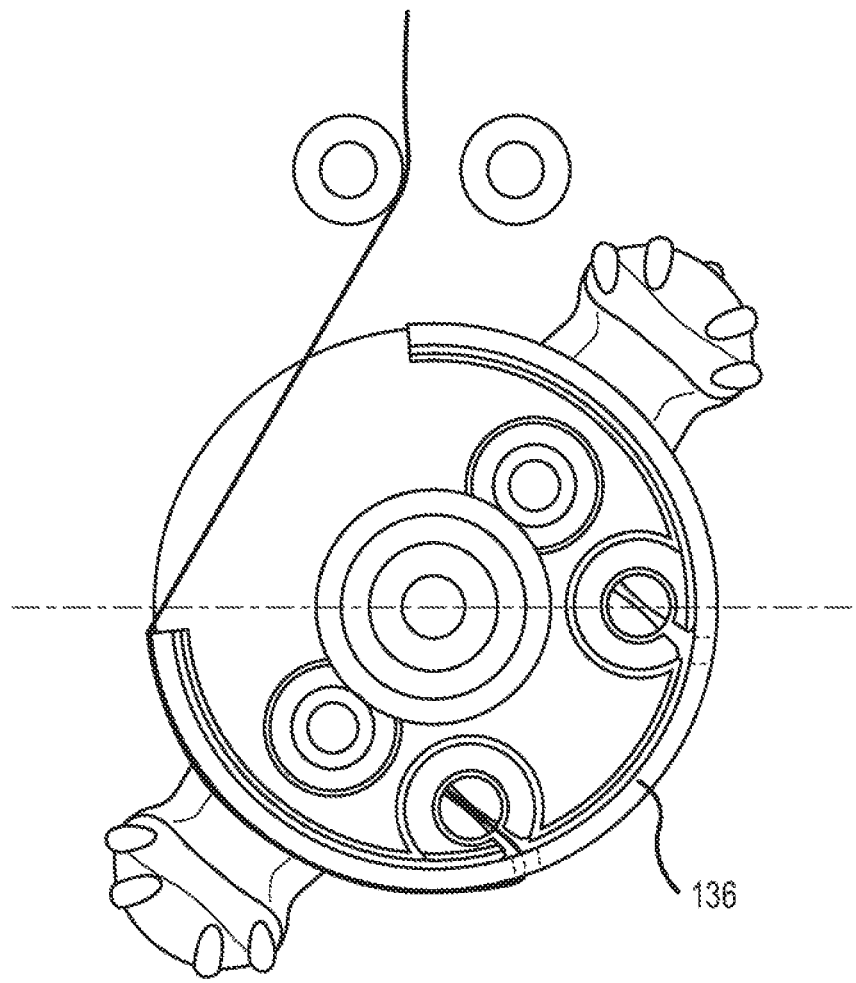

FIGS. 15-17 depict yet another alternative configuration for the guide wall 136. In these figures, the guide wall is rearward facing (i.e., it curves or bows rearward) and comprises a single, continuous arc of approximately 270 degrees, with a forward-facing gap between the ends of the wall. These figures also schematically depict a rotating actuator base, a central screw pillar, two lateral screw pillars, and an outer actuator. Also schematically shown in these figures are two tensioning mechanisms similar to those previously described. In FIG. 15, the actuator is shown in a neutral position. In FIG. 16, the actuator is shown in a slightly-deflected position. Finally, in FIG. 17, the actuator is shown in a fully-deflected configuration.

Although embodiments of a steering actuator for a deflectable catheter have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material that is said to be incorporated (in whole or in part) by reference herein is incorporated herein only to the extent that the incorporated materials does not conflict with existing definitions, statements, or other disclosure material expressly set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material expressly set forth herein will only be incorporated to the extent that no conflict arises between that incorporated material and the existing disclosure material.

What is claimed is:

1. A steering actuator comprising:
(a) an inner actuator adapted to be rotatably mounted within a catheter handle housing, the inner actuator comprising:
a base plate having a distal edge relative to a neutral position of the inner actuator; an opposing proximal edge; a first lateral edge between the distal and proximal edges and on a first lateral side of the base plate; and a complementary, second lateral edge between the distal and proximal edges and on an opposite, second lateral side of the base plate;
complementary first and second fiber guides attached to or formed as an integral part of the base plate so as to move with the base plate during a rotation of the inner actuator, wherein the first fiber guide is located only along the first lateral edge of the base plate, and is configured to pressingly engage only a first pull wire of a pair of pull wires during rotation of the inner actuator, and wherein the second fiber guide is located only along the second lateral edge of the base plate, and is configured to pressingly engage only a second pull wire of the pair of pull wires during rotation of the inner actuator; and
a pair of tuner mechanisms, each tuner mechanism configured to receive one of the pull wires, and to enable initial adjustment of tension in the respective one of the pull wires; and
(b) an outer actuator attached to the inner actuator, the outer actuator comprising at least one boss,
wherein the first and second lateral edges of the base plate are the outer-most lateral edges of the base plate.

2. A steering actuator comprising:
(a) an inner actuator rotatably mounted within a catheter handle housing, the inner actuator comprising:
complementary first and second fiber guides, wherein each fiber guide is contoured against a respective pull wire to change the tension of the respective pull wire in response to rotation of the inner actuator; and
at least one tension mechanism, each tension mechanism comprising a respective tension adjustment pin configured to enable initial tension adjustment of the respective pull wire; and
(b) a user-manipulatable actuator attached to the inner actuator to facilitate user rotation of the inner actuator,
wherein the first and second fiber guides are located only along an outer-most lateral edge of the inner actuator.

3. A control handle comprising the following:
(a) a handle housing;
(b) a first curved, pull-wire-deflection surface mounted to the housing; and
(c) a steering actuator at least partially sandwiched within the handle housing and configured to apply tension to a first pull wire and to a second pull wire, wherein the steering actuator comprises the following:
(i) a first actuator component pivotably mounted within the handle housing, the first actuator component comprising the following:

complementary first and second fiber guides, wherein each fiber guide is configured to affect a pull wire path length traveled by one of the first and second pull wires during actuation of the steering actuator; and first and second anchor points, wherein the first pull wire is affixed to the first actuator component at the first anchor point, and wherein the second pull wire is affixed to the first actuator component at the second anchor point, and wherein the first and second anchor points are configured to adjust the tension of the first and second pull wires; and (ii) a second actuator component attached to the first actuator component, the second actuator component comprising at least one boss, wherein the first and second fiber guides are located only along an outer-most lateral edge of the first actuator.

4. The control handle of claim 3, wherein the first actuator component and the second actuator component comprise a unitary component.

5. The control handle of claim 3, wherein the handle housing comprises a handle upper housing and a handle lower housing; wherein the steering actuator is at least partially sandwiched between the handle upper housing and the handle lower housing; wherein the first anchor point includes a first tensioning mechanism comprising a first tension adjustment pin and a first pin block; and wherein the first tension adjustment pin is rotatably attached to the first pin block, whereby the first tensioning mechanism is adapted to adjust tension in the first pull wire during assembly of the control handle via rotation of the first tension adjustment pin relative to the first pin block.

6. The control handle of claim 3, further comprising an outer knob operable to releasably hold tension applied to the first pull wire by the steering actuator.

7. The control handle of claim 3, wherein the first curved, pull-wire-deflection surface comprises an outer surface of a first roller positioned between a distal end of the handle housing and the first fiber guide.

8. The control handle of claim 7, wherein the first fiber guide comprises one of an arc wall section, a C-shaped wall, a U-shaped wall, a flattened-semicircular-shaped wall, a semicircular-shaped wall, or a horseshoe-shaped wall.

9. A catheter comprising the following:

a longitudinally-extending catheter shaft comprising a proximal end portion and a distal deflectable section;

a handle attached to the proximal end portion of the catheter shaft, the handle including a handle housing;

a first pull wire extending along the catheter shaft and comprising a distal end portion configured to be attached to the distal deflectable section of the catheter shaft, and a proximal end portion; and a steering actuator comprising an inner actuator pivotally mounted within the handle housing, wherein the inner actuator comprises a first guide wall and a first anchor point, wherein the first anchor point is an integral part of, or is mounted on, the inner actuator for rotation therewith, wherein the first pull wire is fixedly attached to the first anchor point, and wherein the first guide wall is configured to affect a pull-wire-path length traveled by the first pull wire during actuation of the steering actuator whereby the steering actuator is operable to tension the first pull wire to thereby deflect the distal deflectable section of the catheter shaft, wherein the first guide wall is located only along an outer-most lateral edge of the steering actuator.

10. The catheter of claim 9, wherein the steering actuator further comprises an outer actuator including at least one boss adapted to receive user input to effect deflection of the distal deflectable section of the catheter shaft.

11. The catheter of claim 9, wherein the first anchor point comprises a first tuner mechanism, including a first tuning pin and a first pin block.

12. The catheter of claim 9, wherein the proximal end portion of the first pull wire traverses the first guide wall and is attached to the first anchor point on the inner actuator.

13. The catheter of claim 9, further comprising a first fiber including a proximal end portion and a distal end portion, wherein the first fiber distal end portion is connected at a first connection point to the proximal end portion of the first pull wire, wherein the first fiber traverses the first guide wall, and wherein the first fiber proximal end portion is attached to the first anchor point on the inner actuator.

14. The catheter of claim 13, wherein a first crimp connects the first fiber distal end portion to the proximal end portion of the first pull wire.

15. The catheter of claim 13, further comprising a first deflection surface attached to the handle housing and positioned between the first connection point and the first guide wall, the first deflection surface being configured to redirect the first fiber as the first fiber extends from the first anchor point to the first connection point.

16. The catheter of claim 15, wherein the first deflection surface comprises an outer cylindrical surface of a first fixed or rotatable roller.

17. The catheter of claim 9, wherein the first guide wall is selected from the group consisting of an arc wall section, a C-shaped wall, a U-shaped wall, a flattened-semicircular-shaped wall, a semicircular-shaped wall, or a horseshoe-shaped wall.

18. The catheter of claim 9, further comprising a locking mechanism operable to hold the distal deflectable section of the catheter shaft in a deflected configuration, wherein the locking mechanism comprises a threaded screw and a threaded knob that are together operable to selectably adjust friction between the steering actuator and the handle housing.

19. The catheter of claim 18, wherein the threaded screw comprises a central screw that the handle housing prevents from rotating, wherein the threaded knob comprises an outer knob, wherein rotation of the outer knob in a first direction increases friction between the steering actuator and the handle housing, and wherein rotation of the outer knob in a second, opposite direction decreases friction between the steering actuator and the handle housing.

20. The catheter of claim 19, wherein the handle housing further comprises first and second travel confinement channels, and wherein the outer knob further comprises a first limit post configured to ride in the first travel confinement channel and a second limit post configured to ride in the second travel confinement channel.

21. The catheter of claim 19, wherein the locking mechanism further comprises a plurality of washers mounted on the central screw, and wherein at least one of the plurality of washers is configured to apply a preload to the steering actuator.

* * * * *